United States Patent
Danziger et al.

(10) Patent No.: US 11,690,338 B2
(45) Date of Patent: Jul. 4, 2023

(54) *CRASPEDIA* PLANT DCRAGLFBIM

(71) Applicant: Danziger DAN' Flower Farm, Beit Dagan (IL)

(72) Inventors: Gavriel Danziger, Beit Dagan (IL); Amir Zuker, Beit Dagan (IL); Yotam Yitzhaki, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 17/540,898

(22) Filed: Dec. 2, 2021

(65) Prior Publication Data

US 2023/0172135 A1  Jun. 8, 2023

(51) Int. Cl.
*A01H 6/14* (2018.01)
*A01H 5/02* (2018.01)

(52) U.S. Cl.
CPC ............... *A01H 6/14* (2018.05); *A01H 5/02* (2013.01)

(58) Field of Classification Search
None
See application file for complete search history.

(56) References Cited

PUBLICATIONS

Berbee Young Plants 2022 Young Plants Catalog (Fall 21-Spr 22) retrieved from the Internet at https://www.berbeeyoungplants.com/catalog/Fall%2021-%20Spr%2022%20BP%20Catalog.pdf, 2 introductory p. pp. 22-24, 33. (Year: 2022).*

Chiu Greenhouse Canada 2021 retrieved from the Internet at https://www.greenhousecanada.com/new-annual-highlights-for-2021-2022/, 15 pp. (Year: 2021).*

* cited by examiner

*Primary Examiner* — June Hwu
(74) *Attorney, Agent, or Firm* — Cassandra Bright

(57) ABSTRACT

The invention relates to the field of Craspedia *globosa*, specifically, the variety designated 'DCRAGLFBIM'. The variety 'DCRAGLFBIM' is characterized by its compact plant habit, improved rooting and abundant flowers. The present invention relates to plant parts, including cells and any propagative material of the new variety 'DCRAGLFBIM', and use of any of the plant parts for reproducing the new variety 'DCRAGLFBIM'. The present invention relates to methods using any plant parts or progeny of 'DCRAGLFBIM' for the purpose of deriving additional new Craspedia varieties. The present invention relates to seed, plants and plant parts produced by crossing 'DCRAGLFBIM' with any other Craspedia variety or other plant. The present invention also relates to methods to produce new varieties of Craspedia *globosa* using the variety 'DCRAGLFBIM' and applying plant breeding techniques.

9 Claims, 3 Drawing Sheets
(2 of 3 Drawing Sheet(s) Filed in Color)

Bulk Method  CR-9-58 → CR-12-165 → CRB-13-200 (Golf Beauty, DCRAGOLFBY, PP30558) → CRB-16-216 (DCRAGLFBIM)

FIG. 3

CRASPEDIA PLANT DCRAGLFBIM

FIELD OF THE INVENTION

The present invention relates to a new, distinct and stable variety of Craspedia globosa, hereinafter referred to as 'DCRAGLFBIM'. The present invention relates to seeds which are the Craspedia globosa 'DCRAGLFBIM', as well as, plants and plant parts produced by these seeds which have all of the morphological and physiological characteristics of the Craspedia globosa 'DCRAGLFBIM'. The present invention also relates to methods for producing these seeds and plants of the Craspedia globosa 'DCRAGLFBIM'. Furthermore, the present invention relates to a method of producing progeny Craspedia plants by crossing Craspedia 'DCRAGLFBIM', as either the female or seed or male or pollen parent, with another Craspedia plant and selecting progeny.

BACKGROUND OF THE INVENTION

The present invention relates to a new, distinct and stable variety of Craspedia globosa, and hereinafter referred to by the variety denomination 'DCRAGLFBIM'. The new Craspedia 'DCRAGLFBIM' originated from a crossing made in a controlled breeding program by the inventor in Spring of 2015, and selected in Spring of 2016, in Mishmar Hashiva, Israel. The parent is the Craspedia globosa proprietary line identified by code 'CRB-13-200' and 'DCRAGOLFBY', USPP 30, 558.

The new variety was selected from the F4 generation, the method was by bulk breeding. The new variety is observed to have 87.5 homozygosity to the claimed properties of better rooting and earlier flowering. The breeding scheme can be found in FIG. 3

Craspedia is a member of the Asteraceae family. Craspedia globosa is a vascular land plant, native to Australia and New Zealand. For the most part, plants of Craspedia globosa are perennial, however, often produced as an annual for commercial purposes. The synonym Pycnosorus is also used to identify this Genus.

Craspedia globosa are known to be useful as cut flowers or garden plants.

Plants of Craspedia are tufting and produce flower stalks of hemispherical compound capitula borne on erect, unbranched scapes. Individual florets are evenly spaced, and nearly cylindrical.

Asexual propagation of Craspedia can be performed by vegetative cuttings and plant division, however, propagation is most commonly performed by sowing seeds.

The Craspedia globosa seeds and plants produced by this method are uniform with respect their morphological and physiological characteristics.

Methods for cultivation and crossing of Craspedia are not well known. Commercial seed suppliers advertise Craspedia globosa under the commercial names Sun Ball, Billy Buttons and Drumstick Flower. It is assumed all of these commercial names refer to the same unpatented cultivar of Craspedia globosa.

A basic reference to the species can be found in: Electronic Flora of South Australia species Fact Sheet, database (version 2007), which is herein incorporated by reference. This reference gives a basic botanical description of Craspedia globosa. Scientific literature of Craspedia globose is not readily available.

A need exists for a greater variety of Craspedia cultivars with improved commercial features. The new Craspedia 'DCRAGLFBIM' was developed through a controlled breeding program and exhibits unique, desirable and stable characteristics.

Craspedia globosa, also known as "Drumstick Flower", is valued as an ornamental plant useful for cut flower production as well as garden use. Whilst reducing the present invention to practice, the present inventors were able, to generate a unique variety of Craspedia globosa.

SUMMARY OF THE INVENTION

The present invention provides Craspedia plant selections that produce compact plants which root well. Commercial production of Craspedia globosa has been hindered by poor rooting. The new variety described herein roots more easily and successfully than known varieties. Additionally, the new variety begins flowering early. These qualities distinguish the new cultivar from typical Craspedia globosa varieties.

These and other objectives have been achieved in accordance with the present invention which provides 'DCRAGLFBIM' as a new Craspedia cultivar that is a product of a planned breeding program conducted by the inventors. The parent is the Craspedia globosa inbred line identified by code CRB-13-200 'DCRAGOLFBY', USPP 30,558.

The parental cultivar has a sufficient degree of homozygosity such that the progeny of the cross are genotypically and phenotypically uniform. The new Craspedia globosa 'DCRAGLFBIM' therefore can be produced by sexual reproduction by crossing the parent inbred line 'DCRAGOLFBY', USPP 30,558_to produce a population of progeny plants, each of which has the combination of characteristics as herein disclosed for the new Craspedia globosa 'DCRAGLFBIM'.

Seeds which are variety 'DCRAGLFBIM' are produced by crossing the parental inbred line identified by the code CRB-13-200 and 'DCRAGOLFBY' and USPP 30,558 and which have been deposited Mar. 3, 2022 with the National Collection of Industrial Food and Marine Bacteria(NCIMB), Ferguson Building, Bucksburn, Aberdeen, Scotland, AB21 7 GB a Budapest Treaty recognized depository which affords permanence of the deposit.

Objects of the Invention

The following embodiments and aspects thereof are described in conjunction with system, tools and methods which are meant to be exemplary, not limiting in scope The present invention, in some embodiments thereof, relates to Craspedia globosa plants as well as parts and uses of these plants.

The present invention provides Craspedia plant selections with compact plant habits, improved rooting and abundant flowering. These characteristics in combination distinguish the new cultivar from typical Craspedia globosa varieties.

These and other objectives have been achieved in accordance with the present invention which are the product of a planned breeding program conducted by the inventors. One embodiment of this invention is the Craspedia variety 'DCRAGLFBIM' described herein.

Seeds which can be used to produce the variety DCRAGLFBIM' as has been deposited with the National Collection of Industrial Food and Marine Bacteria_(NCIMB), Ferguson Building, Bucksburn, Aberdeen, Scotland, AB219YA, on Mar. 3, 2022 and having deposit number NCIMB 43945.

Another embodiment relates to a plant produced from seeds which are Craspedia globosa 'DCRAGLFBIM'.

Another embodiment relates to a plant produced by vegetative means which are Craspedia globosa 'DCRAGLFBIM'. The present invention also relates to plant parts, such as pollen, seeds or inflorescences and individual flowers produced by Craspedia globosa 'DCRAGLFBIM'.

Another embodiment relates to a method of producing seed which are Craspedia globosa 'DCRAGLFBIM'.

Another embodiment also relates to a method of producing plants having all the physiological and morphological characteristics of the Craspedia globosa 'DCRAGLFBIM'. comprising the steps of (a) self-pollinating Craspedia globosa 'DCRAGLFBIM'. (b) harvesting seeds produced from said cross; and (c) producing plants from said harvested seeds.

The present invention also relates to producing progeny plants from the cross of Craspedia globosa 'DCRAGLFBIM', as the female or male parent, with another Craspedia or other plant, and selecting progeny plants from this cross.

The present invention also relates to producing progeny plants of Craspedia globosa 'DCRAGLFBIM', by any means of vegetative propagation.

The present invention also relates to producing progeny plants of Craspedia globosa 'DCRAGLFBIM', from natural or induced mutation.

Another embodiment relates to tissue culture produced from protoplast of cells from the Craspedia plant disclosed in the subject application, wherein said cells or protoplasts are produced from a plant part selected from the group consisting of pollen, ovules, embryos, protoplasts, meristematic cells, callus, leaves, anthers, cotyledons, hypcotyl, pistils, roots, root tips, flowers, seeds, petiole and stems.

Another embodiment relates to a plant or a part thereof, produced by growing Craspedia globosa 'DCRAGLFBIM', wherein the plant part comprises at least one cell of Craspedia globosa 'DCRAGLFBIM'.

Another embodiment relates to tissue or cell culture of regenerable cells produced from the plants of Craspedia globosa 'DCRAGLFBIM'. This includes a Craspedia globosa plant regenerated from the tissue or cell culture of Craspedia globosa 'DCRAGLFBIM'.

Another embodiment relates to a method of vegetatively propagating the plant Craspedia globosa 'DCRAGLFBIM' comprising the steps of: collecting tissue or cells capable of being propagated from a plant of Craspedia globosa 'DCRAGLFBIM'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing a Craspedia globosa plant in a Craspedia breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the Craspedia plant of Craspedia globosa 'DCRAGLFBIM', or its parts, wherein application of said techniques results in development of an Craspedia globosa plant.

A further embodiment relates to a method of introducing a mutation into the genome of Craspedia globosa 'DCRAGLFBIM', and wherein the resulting plant comprises at least one genome mutation and producing plants therefrom.

In addition to the exemplary aspects and embodiments described above, further aspects and embodiments will become apparent by study of the following descriptions.

The cultivar 'DCRAGLFBIM' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DCRAGLFBIM' These characteristics in combination distinguish 'DCRAGLFBIM' as a new and distinct Craspedia cultivar:

1. Compact plant habit.
2. Strong rooting.
3. Abundant flower.

Parent Comparison

Plants of the new cultivar 'DCRAGLFBIM' are similar to plants of the parent in most horticultural characteristics, however, plants of the new cultivar 'DCRAGLFBIM' differ in the following;

1. Plants of the new variety begin flowering earlier than plants of the parent variety.
2. Plants of the new variety exhibit improved rooting qualities than the parent variety. The new variety roots on average 7 days sooner than the parent variety. Under normal production conditions a higher percentage of plants of 'DCRAGLFBIM' root successfully than plants of 'DCRAGOLFBY'.
3. The new variety exhibits 87.5 homozygosity in the above traits.
4. Plants of the new variety are more compact than plants of the parent variety.

Commercial Comparison

Plants of the new cultivar 'DCRAGLFBIM' can be compared to the unpatented commercial variety Craspedia 'DPBALGLOBE'. These varieties are similar in most horticultural characteristics however, 'DCRAGLFBIM' differs in the following:

1. 'DPBALGLOBE' has larger flowers than the new variety.
2. 'DPBALGLOBE' flowers approximately 3 to 5 weeks later than the new variety.
3. 'DPBALGLOBE' produces longer foliage than the new variety.
4. Plants of 'DPBALGLOBE' are taller than plants of the new variety.

BRIEF DESCRIPTION OF THE FIGURES

The patent or application file contains at least one drawing executed in color. Copies of this patent or patent application publication with color drawings will be provided by the Office upon request and payment of the necessary fees.

The accompanying photographs illustrate the overall appearance of the new Craspedia globosa 'DCRAGLFBIM' showing the colors as true as is reasonably possible with colored reproductions of this type. Colors in the photographs may differ slightly from the color values cited in the detailed botanical description which accurately describes the color of 'DCRAGLFBIM'.

FIG. 3 is a diagram of the breeding scheme resulting in the Craspedia variety 'DCRAGLFBIM'.

DETAILED BOTANICAL DESCRIPTION

Figure 1:
FIG. 1 shows a side view perspective of a typical flowering plant of 'DCRAGLFBIM', at approximately 97 days old.
Figure 2:
FIG. 2 shows a side view perspective of typical inflorescences of 'DCRAGLFBIM'.

The present invention was created by the inventors, Gavriel Danziger, Amir Zuker and Yotam Yitzhaki during 2014, and flowered for the first time in 2014 in Mishmar Hashiva, Israel.

This invention is directed to Craspedia plant having all the morphological and physiological characteristics of the variety 'DCRAGLFBIM' produced from seeds which are the product of the self-cross of the Craspedia globosa inbred line identified by code CRB-13-200 and USPP 'DCRAGOLFBY' USPP 30,558. The parent has a sufficient degree of homozygosity such that the progeny of the cross were, and continue to be, phenotypically uniform. The new variety 'DCRAGLFBIM' can therefore be produced by sexual reproduction by crossing of the inbred selection identified by the code CRB-13-200 and DCRAGOLFBY', USPP 30,558_to produce a population of progeny plants, each of which has the combination of characteristics herein disclosed for the new variety 'DCRAGLFBIM'.

'DCRAGLFBIM' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and size of inflorescences can result depending on the growing conditions. Typically, these plants are produced outdoors, and variations in temperature and humidity can produce different results.

The aforementioned photographs, together with the following observations, measurements and values describe the new Craspedia 'DCRAGLFBIM' as grown in a greenhouse in Mishmar Hashiva, Israel, during Summer, under conditions which closely approximate those generally used in commercial practice. Plants of 'DCRAGLFBIM' were grown with day temperatures ranging from about 22° C. to 36° C. and night temperatures ranging from about 12° C. to 23° C. 6 treatments of 3 grams per Liter Alar were given at intervals of 7 days.

Color references are made to the Royal Horticultural Society Colour Chart (RHS), 2005 mini edition, except where general colors of ordinary significance are used. Color values were taken under daylight conditions in a greenhouse Mishmar Hashiva, Israel. The age of the plants of 'DCRAGLFBIM' described is about 108 days from planting a rooted cutting.

BOTANICAL CLASSIFICATION: Craspedia *Globosa*
  Parentage:
  Parent: Craspedia *globosa* inbred line identified by code CRB-13-200 and 'DCRAGOLFBY', USPP 30,558.
  Propagation:
Time to Initiate Roots: 14 to 21 days at approximately 20 to 30° C.
Time for produce a rooted liner: 28 to 35 days at approximately 20 to 30° C.
  Plant:
Growth Habit: Erect
Pot size of plant described: 12 cm.
Height: Approximately 21 cm to top of foliage.
  Approximately 45.5 cm to top of inflorescence.
Plant Spread: 30 cm
Growth Rate: Medium
Branching Characteristics: Basal foliage, no branching.
  Foliage:
Leaf:
Arrangement: Rosette
  Average Length: Approximately 18 cm.
  Average Width: Approximately 0.7 cm.
  Shape of blade: Linear
  Apex: Acute
  Base: Clasping
  Attachment: Sessile
  Margin: Involute
  Texture of top surface: Sericeous
  Texture of bottom surface: Sericeous
  Appearance of top surface: Matte
  Appearance of bottom surface: Matte Color:
  Young foliage upper side: NEAR RHS Green N138B
  Young foliage under side: NEAR RHS Green138B
  Mature foliage upper side: NEAR RHS Green 138C
  Mature foliage under side: NEAR RHS Green138C
  Venation:
  Type: Parallel
  Venation color upper side: NEAR RHS Green 138C
  Venation color under side: NEAR RHS Green 138C
  Inflorescence:
Natural flowering season: All around the year in Israel.
Time to flowering from rooted cutting: Approximately 6-8 weeks
Rate of flower opening: Approximately 10-14 days from bud to fully opened flower.
Approximate quantity of flowers per plant: 3 mature inflorescences, with yellow color and 2 immature inflorescences on the described plant.
Inflorescence longevity on plant: Average 38 days
Inflorescence: Spherical capitulum.
  Diameter of entire inflorescence: Average 2.1 cm
  Receptacle shape: Round
  Receptacle height: Average 1.1 cm
  Receptacle diameter: Average 1.1 cm
  Receptacle color: Near RHS Yellow-Green 146D
Bud:
  Bud shape: Spherical.
  Bud length: Approximately 1 cm
  Bud diameter. Approximately 1 cm
  Bud color. Near RHS Yellow-Green 144C
Individual Flowers:
  Diameter of entire flower. Approximately 0.25 cm
  Length of flower: Approximately 0.6 cm
  Petals
  Quantity: 5
  Length: Approximately 0.1 cm
  Width: Approximately 0.1 cm
  Shape: Tubular
  Apex shape: Acute narrowly
  Base: Acute
  Margin: Entire
  Color:
    When opening:
      Upper surface: Near RHS Yellow 12A
      Lower surface: Near RHS Yellow 12A
    Fully opened:
      Upper surface: Near RHS Yellow 12A
      Lower surface: Near RHS Yellow 12A
    Flower Color Fading: NEAR 7A RHS
Bracteole:
  Quantity: 5 per flower
  Length: Approximately 0.5 cm Diameter: Approximately 0.15
　Shape: Spatulate
　Texture: Sericeous
　Color: Near RHS Yellow 2D
Phyllaries/Involucral Bracts: Not Present.
Peduncle:
　Length: Longest average 41 cm. Shortest average 30.5 cm
　Diameter: Approximately 0.3 cm.
　Texture: Sericeous
　Color: Near RHS Green N138C
　Orientation: Approximately 90 degree angle from rosette. Straight.
　Fragrance: Not fragrant
　Reproductive Organs:
Stamens:
　Number: 1
Anthers:
　Shape: Tubular
　Length: Approximately 0.15 cm.
　Color: Near RHS Yellow 12A
　Pollen:
　Color: Near RHS Yellow 12A
　Quantity: Abundant
Pistil:
　Number: 1
　Length: Approximately 0.3 cm.
　Style:
　Length: 0.1 cm
　Color: Near RHS Yellow 12A
　Stigma:
　Shape: Bilobed
　Color: Near RHS Yellow 12A
　Ovary Color: Near RHS Yellow-Green 144C
　Temperature tolerance: Tolerates a range from approximately 5 to 10° C. to 30-35° C.
　Drought tolerance: Drought tolerance observed.
　SEEDS/FRUIT: Achene, of Approximately 4 mm.
　DISEASE/PEST RESISTANCE AND SUSCEPTIBILITY: Neither Resistance Nor susceptibility to normal diseases and pests of Craspedia observed.

We claim:

1. A plant of Craspedia 'DCRAGLFBIM', representative seeds having been deposited at the NCIMB in Aberdeen, Scotland AB219YA, on Mar. 3, 2022 and having deposit number NCIMB 43945.

2. A plant or a plant part thereof produced by growing the plant of claim 1, wherein the plant or plant part comprises at least one cell of Craspedia 'DCRAGLFBIM'.

3. A Craspedia plant or part thereof, having the physiological and morphological characteristics of the plant of claim 1.

4. A tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing Craspedia progeny comprising the steps of (a) crossing a plant of Craspedia 'DCRAGLFBIM' as a female or male parent with another Craspedia plant or other plant and (b) selecting progeny.

7. The method according to claim 6, wherein the second plant is another plant of Craspedia 'DCRAGLFBIM'.

8. A Craspedia seed that produces the Craspedia plants of claim 1.

9. A method for developing a Craspedia plant in a plant breeding program using plant breeding techniques, applied to a plant of Craspedia variety 'DCRAGLFBIM' or a part thereof; the method comprising a technique selected from crossing, recurrent selection, backcrossing, pedigree breeding, market enhanced selection, haploid production, double haploid production, transformation, or mutation breeding, wherein said mutation breeding selects for a mutation that is spontaneously or naturally induced or artificially induced, thereby developing a Craspedia plant derived from variety 'DCRAGLFBIM'.

* * * * *